US010867252B2

(12) United States Patent
Lindén

(10) Patent No.: US 10,867,252 B2
(45) Date of Patent: Dec. 15, 2020

(54) CONTINUOUS CALIBRATION BASED ON PUPIL CHARACTERISTICS

(71) Applicant: Tobii AB, Danderyd (SE)

(72) Inventor: Erik Lindén, Danderyd (SE)

(73) Assignee: Tobii AB, Danderyd (SE)

(*) Notice: Subject to any disclaimer, the term of this patent is extended or adjusted under 35 U.S.C. 154(b) by 202 days.

(21) Appl. No.: 16/230,955

(22) Filed: Dec. 21, 2018

(65) Prior Publication Data

US 2019/0130297 A1  May 2, 2019

Related U.S. Application Data

(63) Continuation-in-part of application No. 16/124,776, filed on Sep. 7, 2018.

(60) Provisional application No. 62/556,116, filed on Sep. 8, 2017.

(51) Int. Cl.
A61B 3/113 (2006.01)
G06N 7/00 (2006.01)
A61B 3/14 (2006.01)
A61B 3/00 (2006.01)
A61B 3/11 (2006.01)

(52) U.S. Cl.
CPC ............ G06N 7/005 (2013.01); A61B 3/0025 (2013.01); A61B 3/112 (2013.01); A61B 3/113 (2013.01); A61B 3/14 (2013.01)

(58) Field of Classification Search
CPC ........... A61B 3/14; A61B 3/0025; A61B 3/12; A61B 3/102; A61B 3/0058
USPC ........................................................ 351/206
See application file for complete search history.

(56) References Cited

U.S. PATENT DOCUMENTS 5,270,748 A   12/1993 Katz
10,713,814 B2 * 7/2020 De Villers-Sidani ......................
                                                              G06F 3/011
2003/0086057 A1  5/2003 Cleveland
2003/0123027 A1  7/2003 Amir et al.
2003/0223037 A1  12/2003 Chernyak
2010/0328444 A1  12/2010 Blixt et al.
2014/0211995 A1  7/2014 Model
(Continued)

FOREIGN PATENT DOCUMENTS

EP   3153092 A1   4/2017
EP   3453317 A1   3/2019
(Continued)

OTHER PUBLICATIONS

Non-Final Office action dated Mar. 17, 2020 in U.S. Appl. No. 16/124,776, all pgs.
(Continued)

Primary Examiner — Mohammed A Hasan
(74) Attorney, Agent, or Firm — Kilpatrick Townsend & Stockton LLP

(57) ABSTRACT

A method for forming an offset model is described. The offset model represents an estimated offset between a limbus center of a user eye and a pupil center of the user eye as a function of pupil size. The approach includes sampling a set of limbus center values, sampling a set of pupil center values, and sampling a set of radius values. The offset model is formed by comparing a difference between the set of limbus center values and the set of pupil center values at each of the radius values. A system and a computer-readable storage device configured to perform such a method are also disclosed.

20 Claims, 9 Drawing Sheets

(56) References Cited

U.S. PATENT DOCUMENTS

2017/0112378 A1\* 4/2017 Tamkin .................. A61B 3/154
2019/0076014 A1 3/2019 Ryan et al.

FOREIGN PATENT DOCUMENTS

WO 2005/046465 A1 5/2005
WO 2013/067230 A1 5/2013

OTHER PUBLICATIONS

Extended European Search Report dated Jan. 16, 2019 in related foreign matter EP 18193092.6, 218 pgs.

\* cited by examiner

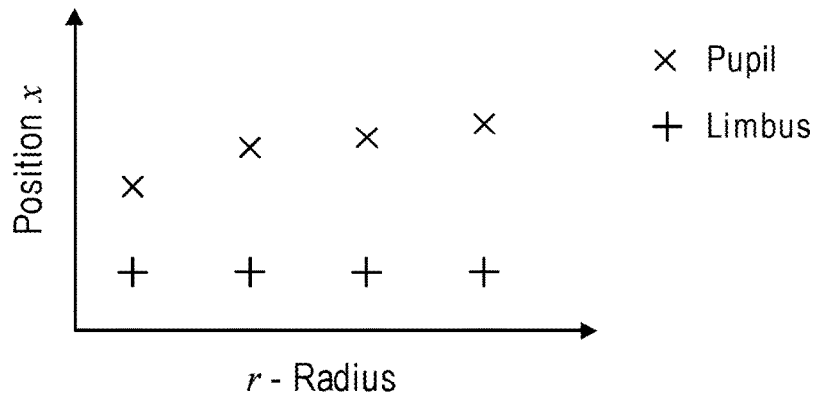
Fig. 10a
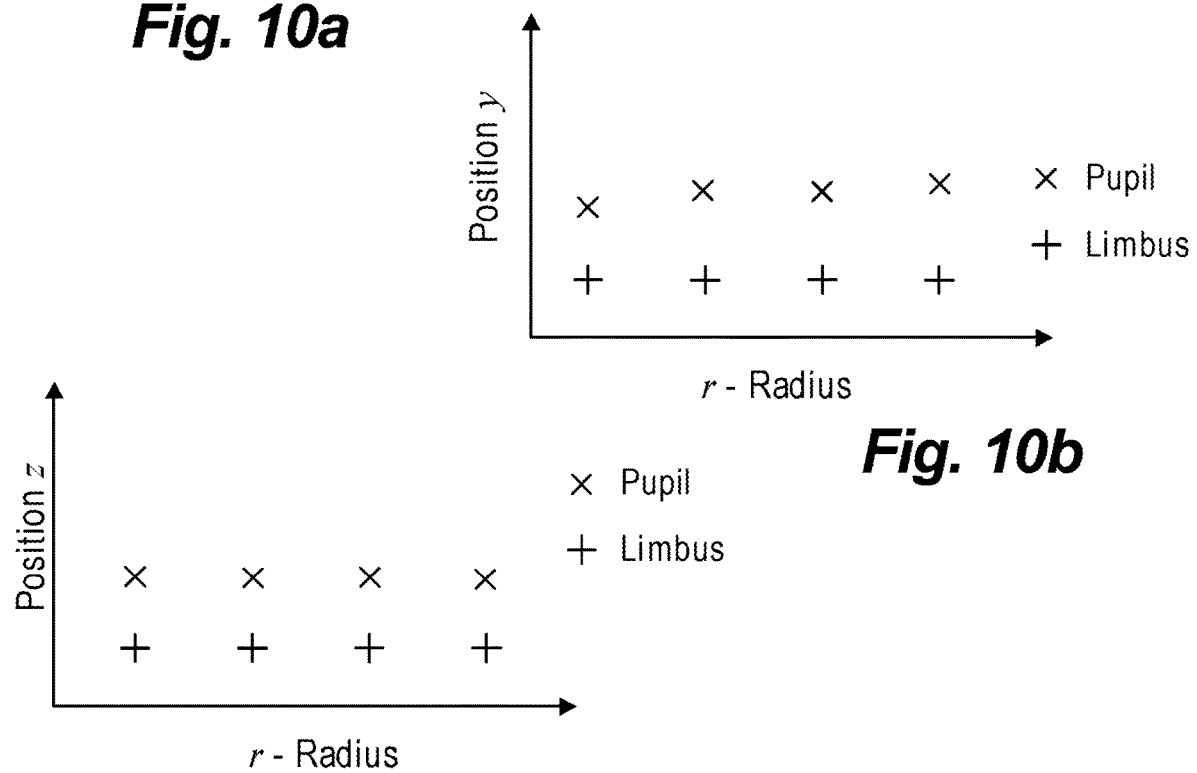
Fig. 10b
Fig. 10d
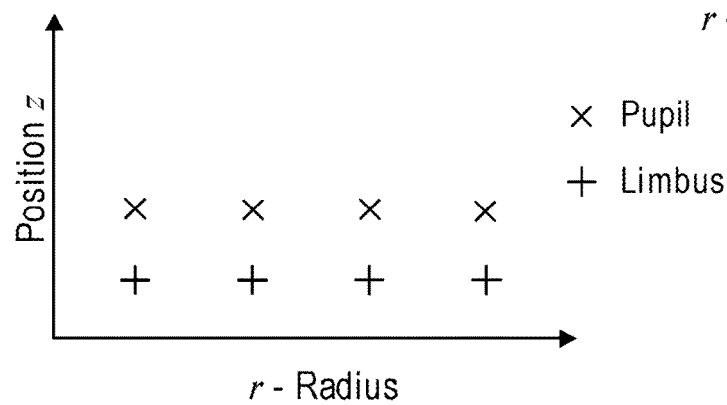
Fig. 10c

CONTINUOUS CALIBRATION BASED ON PUPIL CHARACTERISTICS

CROSS-REFERENCE TO RELATED APPLICATIONS

This application is a continuation-in-part of U.S. Non-Provisional patent application Ser. No. 16/124,776, filed Sep. 7, 2018, which claims priority to and the benefit of U.S. Provisional Patent Application No. 62/556,116, filed Sep. 8, 2017, the entire disclosures of each are incorporated by reference herein for all purposes.

BACKGROUND

Gaze tracking can be performed by measuring where the pupil is located in relation to the cornea. The pupil, however, is not physically fixed in relation to the cornea. Thus, when the pupil expands and contracts it moves with respect to the cornea. This movement can lead to inaccurate eye tracking. This is especially true in different light conditions (e.g., when ambient light oscillates between bright and dim).

BRIEF SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general aspect includes a computer-implemented method, including: determining, according to a sampling rate, a set of limbus center values of a limbus of a user eye. The computer-implemented method also includes determining, according to the sampling rate, a set of pupil center values of a pupil of the user eye. The computer-implemented method also includes determining, according to the sampling rate, a set of radius values of the pupil. The computer-implemented method also includes forming an offset model based on (i) the set of limbus center values, (ii) the set of pupil center values, and (iii) the set of radius values, the offset model describing an estimated offset between a limbus center and a pupil center as a function of pupil size. Other examples of this aspect include corresponding computer systems, apparatus, and computer programs recorded on one or more computer storage devices, each configured to perform the actions of the methods.

Implementations may include one or more of the following features. The computer-implemented method where: determining the set of limbus center values includes measuring a first limbus center value at a first time and measuring a second limbus center value at a second time. The computer-implemented method may also include determining the set of pupil center values includes measuring a first pupil center value at the first time and measuring a second pupil center value at the second time. The computer-implemented method may also include determining the set of radius values by measuring a first radius value at the first time and measuring a second radius value at the second time. The computer-implemented method where determining the set of limbus center values, determining the set of pupil center values and determining the set of radius values are performed at least while an eye tracking system tracks the user eye. The computer-implemented method where: the offset model includes a linear function. The computer-implemented method may also include forming the offset model by estimating one or more constant values of the linear function based on a linear regression technique. The computer-implemented method where: a first constant value of the one or more constant values corresponds to k parameter of the linear function that represents a slope of the linear function. The computer-implemented method may also include where a second constant value of the one or more constant values corresponds to m parameter of the linear function, the m parameter that represents an intersection point of the linear function. The computer-implemented method where: the method further includes determining a set of offset values by comparing the set of limbus center values with the set of pupil center values, each offset value representing an offset between a respective pupil position with respect to a respective limbus position. The computer-implemented method may also include forming the offset model based further on the set of offset values. The computer-implemented method where forming the offset model includes updating one or more constant values of an existing offset model to define the offset model. The computer-implemented method may further include using an eye tracking algorithm to track the user eye based on the offset model. Implementations of the described techniques may include hardware, a method or process, or computer software on a computer-accessible medium.

One general aspect includes a system, including: a memory configured to store computer-executable instructions; and a processor configured to access the memory and execute the computer-executable instructions to at least: determine a set of limbus center values of a limbus of a user eye, determine a set of pupil center values of a pupil of the user eye, determining a set of radius values of the pupil, and forming an offset model based on (i) the set of limbus center values, (ii) the set of pupil center values, and (iii) the set of radius values, the offset model describing an estimated offset between a limbus center and a pupil center as a function of pupil size. Other examples of this aspect include corresponding computer systems, apparatus, and computer programs recorded on one or more computer storage devices, each configured to perform the actions of the methods.

Implementations may include one or more of the following features. The system where: determining the set of limbus center values includes measuring a first limbus center value at a first time and measuring a second limbus center value at a second time. The system may also include determining the set of pupil center values by measuring a first pupil center value at the first time and measuring a second pupil center value at the second time. The system may also include determining the set of radius values by measuring a first radius value at the first time and measuring a second radius value at the second time. The system where: the processor is further configured to determine a set of offset values by comparing the set of limbus center values with the set of pupil center values, each offset value representing an offset between a respective pupil position with respect to a respective limbus position. The system may also include forming the offset model based further on the set of offset values. The system where determining the set of limbus center values, determining the set of pupil center values, and determining the set of radius values are performed at a sampling rate. The system where: the offset model includes a linear function. The system may also include forming the offset model by estimating one or more constant values of the linear function based on a linear regression technique. The system where: a first constant value of the one or more constant values corresponds to k parameter of the linear function that represents a slope of the linear function. The system may also include a second constant value of the one or more constant values that corresponds to m parameter of the linear function, the m parameter represents an intersection point of the linear function. Implementations of the described techniques may include hardware, a method or process, or computer software on a computer-accessible medium.

One general aspect includes one or more computer-readable storage devices including computer-executable instructions that, when executed by one or more processors, cause the one or more processors to perform operations including: determining a set of limbus center values of a limbus of a user eye, determining a set of pupil center values of a pupil of the user eye, determining a set of radius values of the pupil, and forming an offset model based on (i) the set of limbus center values, (ii) the set of pupil center values, and (iii) the set of radius values, the offset model describing an estimated offset between a limbus center and a pupil center as a function of pupil size. Other examples of this aspect include corresponding computer systems, apparatus, and computer programs recorded on one or more computer storage devices, each configured to perform the actions of the methods.

Implementations may include one or more of the following features. The one or more computer-readable storage devices where the operations further include determining a set of offset values by comparing the set of limbus center values with the set of pupil center values, each offset value representing an offset between a respective pupil center value with respect to a respective limbus center value. The one or more computer-readable storage devices where the operations further include, prior to forming the offset model, estimating one or more values for one or more constant parameters of an eye tracking algorithm by at least: graphing the set of offset values and the set of radius values, and estimating the one or more values for the one or more constant parameters based on a linear approximation of the set of offset values and the set of radius values. The one or more computer-readable storage devices where: determining the set of limbus center values includes measuring a first limbus center value at a first time and measuring a second limbus center value at a second time. The one or more computer-readable storage devices may also include determining the set of pupil center values includes measuring a first pupil center value at the first time and measuring a second pupil center value at the second time. The one or more computer-readable storage devices may also include determining the set of radius values by measuring a first radius value at the first time and measuring a second radius value at the second time. The one or more computer-readable storage devices where determining the set of limbus center values, determining the set of pupil center values and determining the set of radius values are performed at least while an eye tracking system tracks the user eye. The one or more computer-readable storage devices where the operations further include using an eye tracking algorithm to track the user eye based on the offset model. Implementations of the described techniques may include hardware, a method or process, or computer software on a computer-accessible medium.

BRIEF DESCRIPTION OF THE DRAWINGS

Examples of the present disclosure are described in conjunction with the appended figures:

FIGS. 10a-10d are graphs showing various data as collected using the techniques of the present disclosure;

Figure 1:
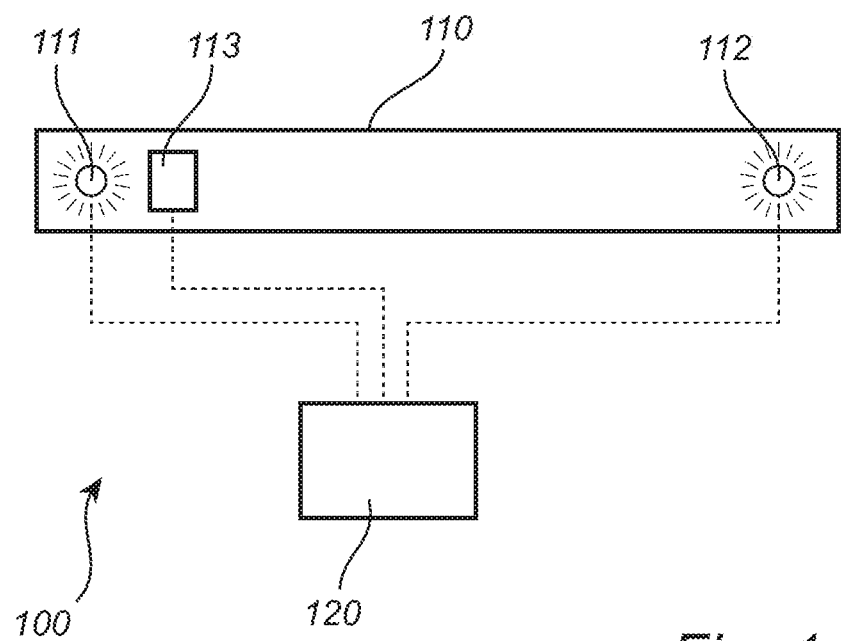
FIG. 1 shows an eye tracking system according to an example of the present disclosure.

All of the figures are schematic and generally only show parts which are necessary in order to elucidate the respective examples, whereas other parts may be omitted or merely suggested.

DETAILED DESCRIPTION

The ensuing description provides exemplary examples only, and is not intended to limit the scope, applicability, or configuration of the disclosure. Rather, the ensuing description of the exemplary examples will provide those skilled in the art with an enabling description for implementing one or more exemplary examples. It being understood that various changes may be made in the function and arrangement of elements without departing from the spirit and scope of the disclosure as set forth herein.

For example, any detail discussed with regard to one example may or may not be present in all contemplated versions of that example. Likewise, any detail discussed with regard to one example may or may not be present in all contemplated versions of other examples discussed herein. Finally, the absence of discussion of any detail with regard to example herein shall be an implicit recognition that such detail may or may not be present in any version of any example discussed herein.

Specific details are given in the following description to provide a thorough understanding of the examples. However, it will be understood by one of ordinary skill in the art that the examples may be practiced without these specific details. For example, circuits, systems, networks, processes, and other elements in the disclosure may be shown as components in block diagram form in order not to obscure the examples in unnecessary detail. In other instances, well-known circuits, processes, algorithms, structures, and techniques may be shown without unnecessary detail in order to avoid obscuring the examples.

Also, it is noted that individual examples may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all examples. A process may correspond to a method, a function, a procedure, a subroutine, a subprogram, etc. When a process corresponds to a function, its termination corresponds to a return of the function to the calling function or the main function.

The term "machine-readable medium" or the like includes, but is not limited to transitory and non-transitory, portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, examples of the disclosure may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

The present disclosure generally relates to the field of eye tracking. In particular, the present disclosure relates to methods and systems for generating and/or using gaze tracking information indicating a gaze direction of an eye.

Several different eye tracking technologies are known in the art. Such technologies may for example be employed to allow a user to indicate a location at visual display by looking at that location. The eye tracking may for example be performed by means of a system that captures images of the user's face and extracts key features from the user's face, such as for example pupil center and glints from illuminators illuminating the user's face. The extracted features may then be employed to determine where at the display the user is looking. Naturally, factors such as accuracy, speed and reliability/robustness of the eye tracking are desirable to achieve a positive user experience. Therefore, several schemes have been proposed for mitigating the negative effects of different types of errors or inaccuracies that may occur in eye tracking systems.

One such example is disclosed in US 2010/0328444 (the entire contents of which are hereby incorporated by reference, for all purposes, as if fully set forth herein), which proposes an eye tracker that includes at least one illuminator for illuminating an eye, at least two cameras for imaging the eye, and a controller. The configuration of the illuminator(s) and cameras is such that at least one camera is non-coaxial with a reference illuminator. The controller is adapted to select camera based on an image quality factor. By performing the camera selection repeatedly, the eye tracking may be based on the one of the two cameras that yields the best quality metric. In this way, the eye tracking becomes less vulnerable to disturbances, such as sight-obscuring objects.

Although such technologies may provide a more robust and accurate tracking of the eye, there is still a need for improved eye tracking systems and methods.

An objective of the present disclosure is to provide a technology allowing for eye tracking methods, systems and devices having an improved performance. Additional and alternative objects may be understood from the following.

The present disclosure relates to a technology in which an angular offset between eye direction and gaze direction of a user's eye may be obtained, e.g. during a calibration procedure, and employed for subsequent tracking of movements of the eye. The eye direction may be understood as a three-dimensional vector defined by the relative position of the cornea and the pupil of the eye. The eye direction may thus be understood as the relative direction of the eye in space, and may also be referred to as the optical axis of the eye. The gaze direction, on the other hand, may be understood as the visual axis, or line of sight, represented by a three-dimensional vector defined by the point of gaze of the user and the foveal region of the eye. The gaze direction often deviates from the eye direction by an angular offset that may be eye/subject dependent. Therefore, the angular offset may be determined in e.g. a calibration procedure, in which the user views an animated or static calibration pattern having one or several points (i.e., points of gaze) having a known position or a movement trajectory, while the eye direction is measured by observing for example pupil location and glints from illuminators illuminating the user's face the. The measured eye direction can then be compared to the known gaze direction of the user viewing for example a calibration pattern.

Hence, according to a first aspect, there is provided method comprising the steps of obtaining a first angular offset between a first eye direction and a first gaze direction of an eye having a first pupil size, obtaining a second angular offset between a second eye direction and a second gaze direction of the eye having a second pupil size, and forming, based on the first angular offset and the second angular offset, a compensation model describing an estimated angular offset as a function of pupil size.

According to a second aspect, there is provided a system comprising a circuitry configured to perform the method steps according to the first aspect, i.e., to obtain a first angular offset between a first eye direction and a first gaze direction of an eye having a first pupil size, obtain a second angular offset between a second eye direction and a second gaze direction of the eye having a second pupil size, and form, based on the first angular offset and the second angular offset, a compensation model describing an estimated angular offset as a function of pupil size.

The eye direction may be determined by observing the pupil position, such as the location of an estimated pupil center, in relation to an estimated cornea center. These two positions give the eye direction, or visual axis of the eye. A problem exists, however, in that as the iris dilates and constricts, the pupil typically does not open and close completely concentrically about a fixed point in the eye. In other words, the estimated pupil center position may vary with the pupil size in a way that may be eye or subject dependent. As a result, the estimated eye direction and hence its angular offset to the gaze direction may vary with the size of the pupil. Thus, by forming a compensation model describing the estimated angular offset as a function of pupil size, this effect can be compensated for and the accuracy of the eye tracking improved. In particular, this allows for a gaze tracking that is less sensitive to errors and deviations associated with varying lighting conditions that affects the pupil size. The present inventive concept is therefore of particular interest in applications utilizing for example dynamic display brightness (such as e.g. virtual reality applications) or used in ambient lighting (such as e.g. augmented reality applications).

In the above, the compensation model is based on two measured points, i.e., the first angular offset for the first pupil size, and the second angular offset for the second pupil size. It is however appreciated that this is merely an illustrating example, and that the model just as well may be based on data sets comprising two or more measured points. Further, the compensation model may be updated in subsequent calibration processes, taking into account further angular offsets associated with further pupil sizes. Thus, the present disclosure is not limited to a compensation model formed from two data points or formed at a specific point in time. It may as well be a dynamic model that is updated whenever relevant data is acquired, or upon request by a user or provider.

As already mentioned, the compensation model may be used for improving the gaze tracking by dynamically adapting the calculation of the gaze direction to the actual size of the pupil. Hence, according to an example, the method may further comprise obtaining a third eye direction of the eye having a third pupil size, and determining, based on the compensation model, an estimated angular offset associated with the third pupil size. This angular offset may then be employed for determining, based on the third eye direction, a third gaze direction of the eye having the third pupil size. The present example may thus represent the method or system during operation, i.e., when the eye tracking technology is employed for determining the gaze direction of the user. In that case, the above described steps of obtaining the third eye direction and determining the gaze direction based on the angular offset of the particular pupil size, may be performed repeatedly during the operation.

According to some examples, the first eye direction and the first pupil size may be obtained from a first image of the eye having the first pupil size, wherein the second eye direction and the second pupil size may be obtained from a second image of the eye having the second pupil size. In one example, the method may include the steps of acquiring the first image and the second image of the eye. These images may e.g. be obtained from one or several image sensors included in the system, or from elsewhere. The pupil size in the respective images may be determined as the size of the pupil as represented in the image, or as the actual pupil size. Using the actual pupil size is advantageous in that the size may not depend on the distance between the eye and the image sensor, or camera.

According to an example, the first image may be acquired at a first illumination intensity and the second image at a second illumination intensity, differing from the first illumination intensity. The illumination intensity may for example be actively changed when capturing the second image, for example by changing a display brightness, so as to obtain calibration data for different pupil sizes. Thus, the change in illumination intensity may be included as an active step in a calibration process. In another example, the capturing of the second image may be triggered by a predetermined change in the illumination intensity, i.e., when a predetermined change in illumination intensity is detected, or when a predetermined change in pupil size is detected.

According to an example, the eye direction may be determined based on a relative position between an estimated cornea center and an estimated pupil center. This may for example be achieved by illuminating the eye with an illuminator, such as e.g. an infrared or near-infrared illuminator, causing at least two reflections or glints on the eye. A two-dimensional image may then be captured and analyzed to determine the positions in the image in which the reflections are located. If the cornea is assumed to have a spherical shape, i.e., such that the observed surface portion of the cornea may be approximated by a segment of a sphere, the positions of the reflections can be used to derive an estimated cornea sphere center in the eye. The estimated pupil center may be derived from an image of the eye, for example based on image analysis in which the boundary between the iris and the pupil. The pupil, as identified in the image, may be projected onto a model of the cornea so as to determine an estimated center of the pupil in the actual eye. The first eye direction and the second eye direction may be then be determined based on the location of the estimated cornea sphere center and the location of an estimated pupil center.

The gaze direction may be defined by a vector in space pointing at the object the user watches. In other words, the gaze direction may be defined by the gaze point and the position of the foveal region of the retina. According to an example, the first gaze direction and the second gaze direction may be determined based on the gaze point of the eye and the location of the estimated cornea sphere center. Advantageously, the gaze point may be a known point in space, such as e.g. a calibration structure having a known location relative to e.g. the image sensor viewing the eye.

The term pupil size may refer to the size of the pupil as represented in an image of the eye, or to the actual size of the pupil or aperture of the eye as defined by the iris. Other definitions are however also conceivable, such as the size of the imaged pupil when projected onto a sphere representing the curvature of the cornea, or the like. The pupil edge pixels in the image may be employed to estimate the position of the center of the pupil, the edge of the pupil and the pupil size (which for example may be determined in terms of a radius of the pupil).

According to an example, the gaze tracking data associated with the eyes having the first pupil size and the second pupil size, respectively, may be stored in a storage area. The storage area may for example form part of the above described system, or be communicatively connected to, but not included in, the system. By storing the gaze tracking data, such as e.g. images of the eyes, from which the eye direction and pupil size may have been retrieved, these data may be reused in subsequent calibration or later adjustment of the compensation model. The stored data could also be referred to as raw data.

Hence, according to an example, the method may comprise the additional steps of obtaining a further angular offset between a further eye direction and a further gaze direction of the eye having a further pupil size, and updating the compensation model based on the stored gaze tracking data, the further pupil size and the further angular offset.

According to an example, the eye tracking system may comprise at least one illuminator for illuminating the eye, and at least one image sensor, or camera, for capturing images of the eye. The illuminator may for example comprise at least two light sources, such as light emitting diodes, arranged to generate at least two glints on the cornea of the eye. The light emitted by the illuminator may in some examples be infrared or near-infrared light.

According to a third aspect, a device that is adapted to be worn by a user is disclosed. The device may e.g. be a virtual reality headset or a pair of augmented reality glasses. The device may comprise at least one illuminator for illuminating an eye of the user, at least one camera for capturing images of the eye, and a circuitry. The circuitry may be configured to obtain a first angular offset between a first eye direction and a first gaze direction of the eye having a first pupil size, obtain a second angular offset between a second eye direction and a second gaze direction of the eye having a second pupil size, and form, based on the first angular offset and the second angular offset, a compensation model describing an estimated angular offset as a function of pupil size.

Examples of the method of the first aspect may be performed by the system of any of the examples of the second aspect, or by the device of the third aspect, or by the circuitry comprised in such systems/devices.

According to a fourth aspect, a computer program product is disclosed, comprising one or more computer-executable instructions that, when executed by a computing system that implements eye/gaze data processing, cause the computing system to perform a method. The method may for example be the method according to the first aspect.

Examples of the one or more computer-readable storage media according to the third aspect may for example include features corresponding to the features of any of the examples of the system according to the second aspect or the device according to the third aspect.

The one or more computer-readable media may for example be one or more non-transitory computer-readable media.

It is noted that examples of the disclosure relate to all possible combinations of features recited in the claims.

The present disclosure relates to a technology in which a positional offset of a user's pupil with respect to limbus center of the eye can be continuously sampled or periodically sampled, e.g., during a calibration procedure such as one supporting continuous calibration of an eye tracking system while this system is being actually used by an end user, and employed for subsequent tracking of movements of the eye. The techniques described herein define a coordinate system that is fixed in the eye, with the origin in the center of the eye and an axis pointing in the direction of the eye (e.g., an eye direction). For example, the origin can be located at the center of an assumed spherical representation of the cornea and the z-axis can extend through the center of the limbus. The center of the pupil can be identified within this coordinate system and represented by a three-dimensional vector. The pupil center differs from the limbus center and may be exaggerated under certain lighting conditions and/or be subject dependent. As the size of the pupil changes, the position of the pupil center within the eye drifts with respect to the fixed-eye coordinate system. In particular, the eye may drift or move downwards and inwards in the direction of the lower portion of the nose. The techniques described herein measure this movement and produce a offset model or parameters for the calibration model to account for such movement.

For example, the techniques described herein can account for this difference as it changes over time with respect to a radius of the pupil. To begin, measurements of the limbus center, pupil center, and pupil radius can be obtained at some sampling rate. These measurements are then used to form an offset model that accounts for the change in pupil location and pupil radius. Parameters of the offset model are used by an eye tracking algorithm to compensate for this change. The offset model, as described herein, has similar characteristics to the compensation model described herein.

The sampling can be performed at any suitable rate and the parameters can be updated at the same rate or a different rate. The techniques described herein can be performed in the background while an eye tracking system is tracking the subject's eyes. In most cases, the subject will not even know that this ongoing and continuous calibration technique is occurring. Because the calibration is performed on an ongoing and continuous basis, there is less interruption to the subject, as compared to dedicated calibration approaches. This results in a more efficient process with less friction as compared to dedicated calibration approaches. This is because the subject is not required to make any selections, click any buttons, page through any user interfaces, or follow some predetermined routine, any of which constitute interruptions to the subject's experience with the eye tracking system.

Additionally, the function of the eye tracking system is improved because the ongoing calibration provides a richer and more complete data set, as compared to dedicated calibration approaches, which results in improved user control of a computer system by means of the eye tracking system. The data set is not only more complete but it is also considerate of context, e.g., specific to the subject and the current conditions such as ambient light and orientation of eye tracking system with respect to the subject. Thus, as updated calibration data is collected, the calibration of the eye tracking system is also updated to account for the current conditions.

The improvements described herein constitute improvements to computer technology because eye tracking systems can be used as an interface means to a computer.

Hence, according to a first aspect, described herein is a method including the operations including, at least, determining, according to a sampling rate, a set of limbus center values of a limbus of a user eye, determining, according to the sampling rate, a set of pupil center values of a pupil of the user eye, determining, according to the sampling rate, a set of radius values of the pupil, and forming an offset model based on (i) the set of limbus center values, (ii) the set of pupil center values, and (iii) the set of radius values, the offset model describing an estimated offset between a limbus center and a pupil center as a function of pupil size.

According to a second aspect, there is provided a system including circuitry configured to perform a process as described in the first aspect.

According to a third aspect, there is provided a device that is adapted to be worn by a user. The device may, for example, be a virtual reality headset or a pair of augmented reality glasses. The device may include at least one illuminator for illuminating an eye of the user, at least one camera for capturing images of the eye, and a circuitry. The circuitry may be configured to perform the process described with respect to the first aspect.

According to a fourth aspect, there is provided a computer-readable storage device configured to store instructions for performing a process as described in the first aspect.

Examples of the method of the first aspect may be performed by the system of any of the examples of the second aspect, or by the device of the third aspect, or by the circuitry comprised in such systems/devices.

Examples of the one or more computer-readable storage media according to the third aspect may for example include features corresponding to the features of any of the examples of the system according to the second aspect or the device according to the third aspect.

The one or more computer-readable media may for example be one or more non-transitory computer-readable media.

It is noted that examples of the disclosure relate to all possible combinations of features recited in the claims.

The above, as well as additional objects, features and advantages of the present disclosure, will be better understood through the following illustrative and non-limiting detailed description, with reference to the appended drawings. In the drawings like reference numerals will be used for like elements unless stated otherwise.

FIG. 1 shows an eye tracking system 100 (which may also be referred to as a gaze tracking system), according to an example. The system 100 may comprise illuminators 111, 112 for illuminating an eye of a user, and an image sensor 113 (which also may be referred to as a light sensor) for capturing images of the eye of the user. The illuminators 111, 112 may for example be light emitting diodes emitting light in the infrared frequency band, or in the near infrared frequency band. The light sensor 113 may for example be a camera, such as a complementary metal oxide semiconductor (CMOS) camera or a charged coupled device (CCD) camera.

A first illuminator 111 may be arranged coaxially with (or close to) the image sensor 113 so that the image sensor 113 may capture bright pupil images of the user's eye. Due to the coaxial arrangement of the first illuminator 111 and the image sensor 113, light reflected from the retina of the eye returns back out through the pupil towards the image sensor 113, so that the pupil may appear brighter than the iris surrounding it in images where the first illuminator 111 illuminates the eye. A second illuminator 112 may be arranged non-coaxially with (or further away from) the image sensor 113 for capturing dark pupil images. Due to the non-coaxial arrangement of the second illuminator 112 and the image sensor 113, light reflected from the retina of the eye does not reach the image sensor 113 and the pupil may appear darker than the iris surrounding it in images where the second illuminator 112 illuminates the eye. The illuminators 111 and 112 may for example take turns to illuminate the eye, so that every second image is a bright pupil image, and every second image is a dark pupil image.

The eye tracking system 100 may also comprise circuitry 120 (for example including one or more processors) for processing the images captured by the image sensor 113. The circuitry 120 may for example be connected to the image sensor 113 and the illuminators 111, 112 via a wired or a wireless connection. In another example, circuitry 120 in the form of one or more processors may be provided on one or more stacked layers below the light sensitive surface of the image sensor 113.

Figure 2:
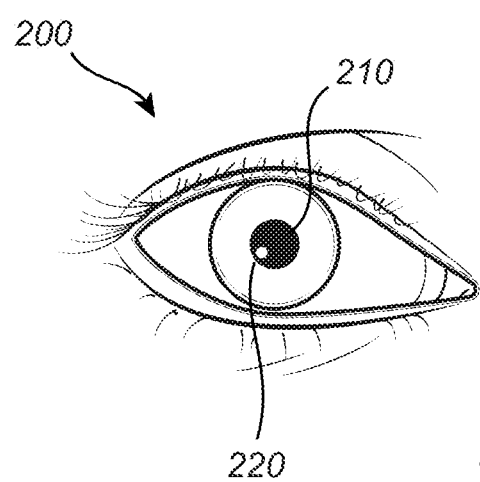
FIG. 2 shows an example image of an eye.

FIG. 2 shows an example of an image of an eye 200, captured by the image sensor 113 as discussed in connection with the system 100 of FIG. 1. The circuitry 120 may for example employ image processing (such as digital image processing) for extracting features in the image. The circuitry 120 may for example be configured to estimate a size of the pupil 210, e.g. in terms of a radius, and the position of a center of the pupil. The circuitry 120 may further be configured to estimate the position of the center of the glints 120 caused by reflection of light from the illuminators 111, 112, and from these positions calculate wherein the user's eye 200 is pointing. Since there is typically an offset between the optical center of the eye 200 and the fovea, the processor performs calibration of the fovea offset to be able to determine where the user is looking. This will be described in more detail with reference to FIGS. 3 and 4.

In the examples described with reference to FIGS. 1 and 2, the illuminators 111, 112 may be arranged in an eye tracking module 110 placed below a display watched by the user. This arrangement serves only as an example. It will be appreciated that more or less any number of illuminators and image sensors may be employed for eye tracking, and that such illuminators and image sensors may be distributed in many different ways relative to the user and any scenes or displays watched by the user. It will be appreciated that the eye tracking scheme described in the present disclosure may for example be employed for remote eye tracking (for example in a personal computer, a smart phone, or integrated in a vehicle) or for wearable eye tracking (such as in virtual reality glasses or augmented reality glasses).

Figure 3:
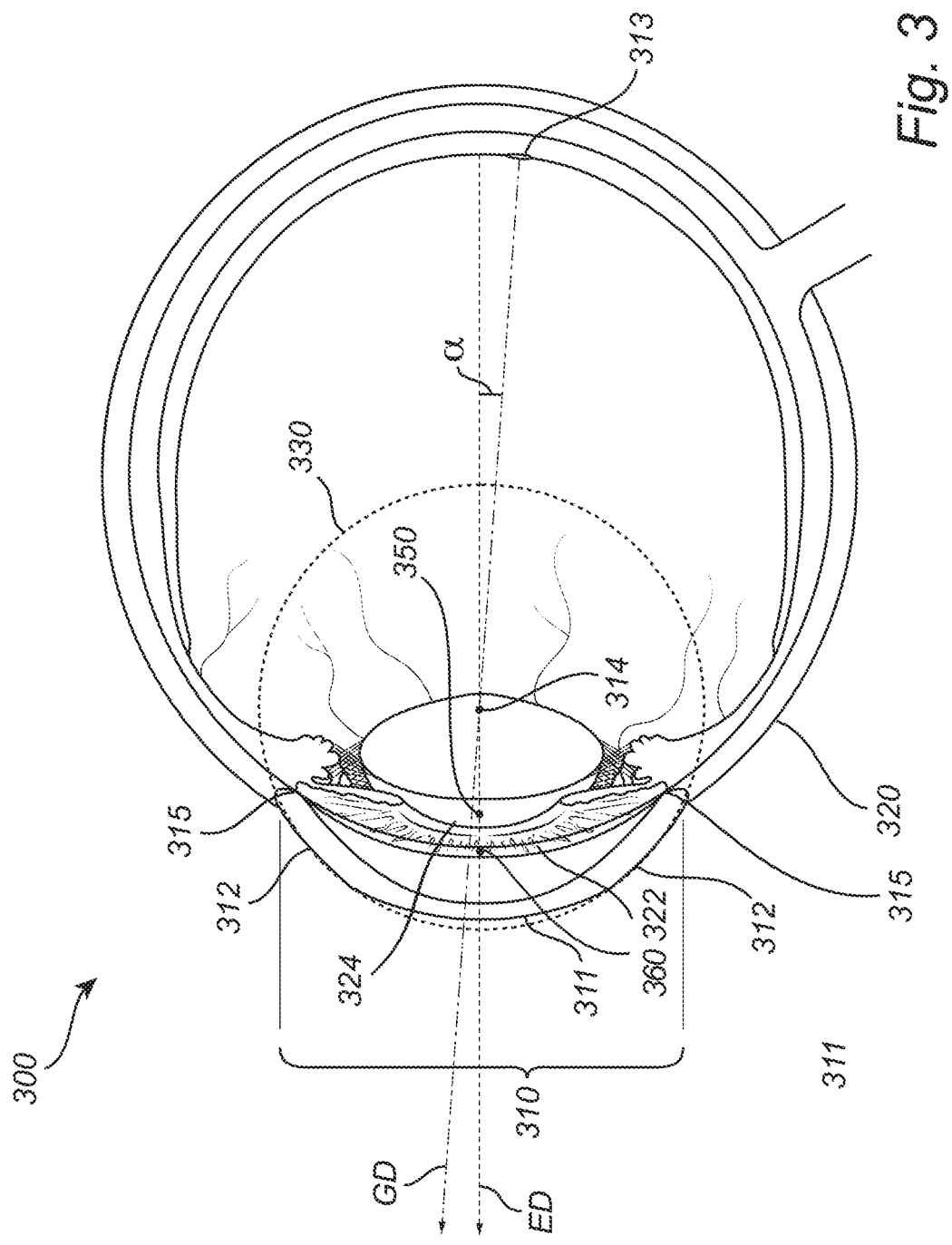
FIG. 3 is a cross sectional view of a part of an eye.

An example of how to determine the eye direction and the angular offset between the eye direction and the gaze direction will now be described with reference to FIG. 3. FIG. 3 shows a cross section of different parts of an eye 300. The cornea 310 has a central region 311 which in general may have a three-dimensional curvature that may be close to spherical, and an outer region 312 which may be less spherical. The cornea 310 may therefore be approximated with a surface portion of sphere 330 (illustrated by a dashed line in the present figure), having an estimated three-dimensional center point 314 located within the eye. In other words, at least a part of the cornea surface of the eye may be approximated with a shape that can be inscribed in, or conform with, a surface portion of an imaginary sphere 330. The center point may also be referred to as the cornea sphere center 314, and may be calculated from the position of the glints 220 on the cornea surface. The cornea sphere center 314 and the estimated location of the pupil center 350 (also determined from image data) define the optical axis, also referred to as the eye direction ED, of the eye 300. As illustrated in FIG. 3, the optical axis ED may extend from the retina through the cornea sphere center 314, the pupil center 350 and the cornea. As the optical axis may be derived from the estimated cornea sphere center 314 and the pupil center 350, it may also vary as the location of the pupil center 350 varies.

Meanwhile, the visual axis, also referred to as the gaze direction GD, extends from the fovea 313, through the cornea sphere center 314. The visual axis may thus be determined by the physical location of the foveal part of the retina and the configuration of the cornea, and may therefore be less sensitive to variations of the pupil size and location. The orientation of the visual axis, or gaze direction GD, may be determined during calibration of the system, when the user watches a point of gaze having a known position.

As depicted, the visual axis GD may deviate from the optical axis ED by an angular offset $\alpha$. This offset may be determined by means of a calibration process, in which the known gaze direction GD is compared to the eye direction ED. Even though the illustrated example shows an angular offset in the plane of the paper, it will be realized that the offset also may be oriented in a direction normal to that plane, or in any combinations thereof. Hence, the angular offset $\alpha$ between the eye direction ED and the gaze direction GD may be represented by a vector indicating the offset for example in the medial-lateral and the cranial-caudal directions of the eyeball.

FIG. 3 also shows a sclera 320, a limbus 315, and an iris 322 of the eye 300. The limbus 315 is the location in the eye 300 where the sclera 320 intersects the iris 322. In other words, the limbus 315 represents the perimeter of the iris 322. The limbus 315 is relatively fixed within the eye 300. The pupil 31 The point in the eye where the sclera 320 meets the 324, however, moves considerably within the eye 300. As described with reference to other figures, the pupil center 350 can be compared to a limbus center 360 (which appear aligned in the view shown in FIG. 3) in order to form the offset model described herein.

Figure 4A:
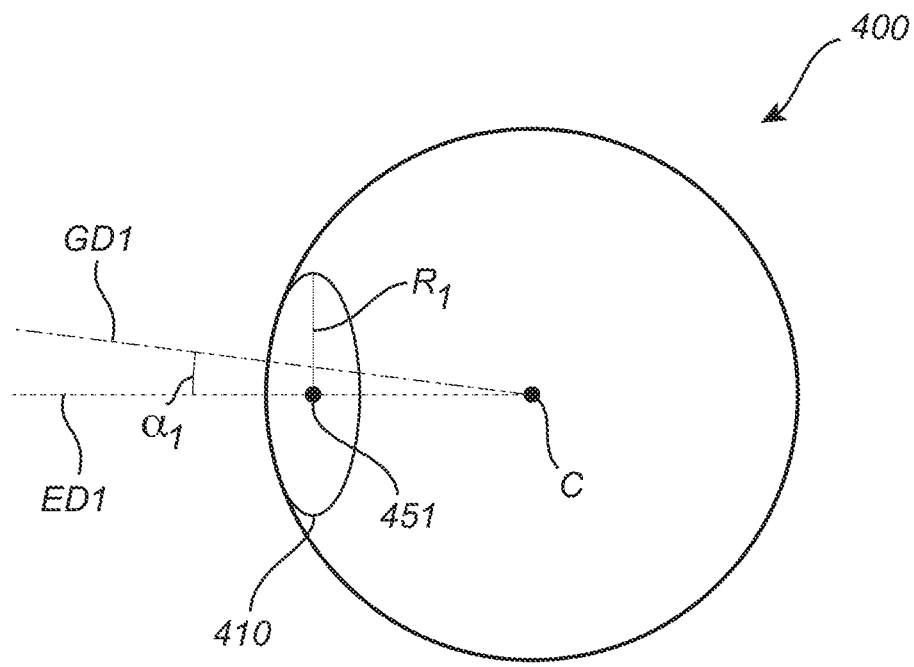
FIGS. 4a-4b are perspective views of an eye having a first pupil size, and the eye having a second pupil size.
Figure 4B:
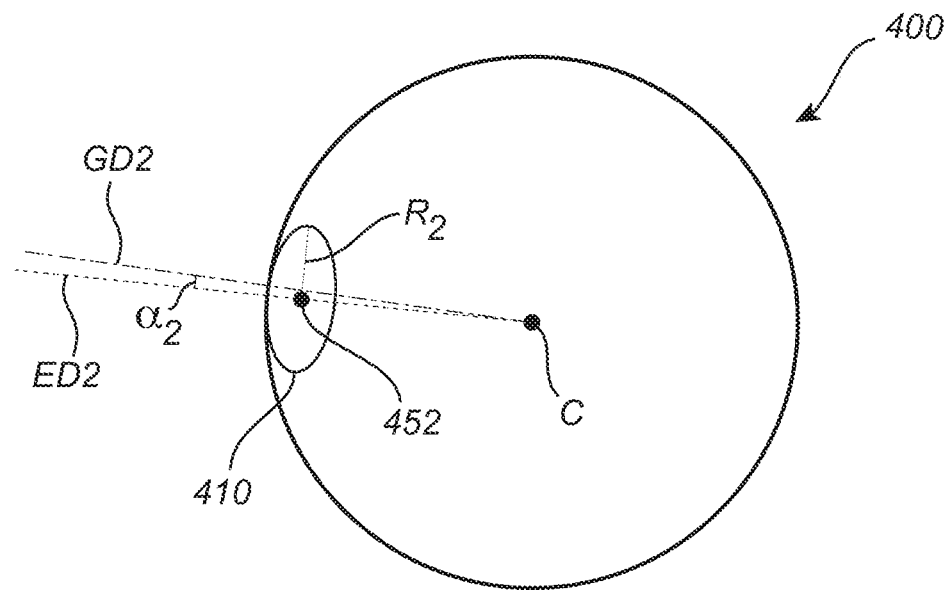

FIG. 4a shows perspective views of an eye 400 wherein the pupil 410 has a first size, or radius, R1. FIG. 4b is a perspective view of the same eye 400 having a second pupil size R2. The pupil size may for example vary with the illumination intensity, where an increase in intensity is known to cause the iris 410 to constrict and a reduction in intensity may cause the iris 420 to dilate. This is a known effect for applications in which the eye is exposed to for example ambient lighting, such as augmented reality applications, or a dynamic display brightness.

The location of the pupil center 451, 452 may shift with the change in pupil size, which thereby may affect the estimated eye direction ED and hence the angular offset used for calculating the gaze direction GD. In the present figures, the shift in the medial/lateral position of the pupil center of the eye is indicated by the angular offset $\alpha_1$, $\alpha_2$, suggesting that the pupil center in the present example is shifted upwards (in the cranial direction) relative to a center point c of the eye as the pupil size is reduced from the first size R1 to the second size R2.

In FIG. 4a the eye 400 has a first, dilated pupil size R1, with the first angular offset $\alpha_1$ between the first eye direction ED1 and the first gaze direction GD1. If the location of the pupil center 451 is shifted, for example due to a constriction of the iris 410, the estimated eye direction ED1 may change as illustrated in FIG. 4b, which shows the eye 400 having a second, constricted pupil size R2 resulting in a second angular offset $\alpha_2$ between the second eye direction ED2 and the second gaze direction GD2. It will be noted that the first and the second eye direction ED1, ED2 therefore may differ from each other due to the shift in pupil center position, whereas the first and second gaze direction GD1, GD2 (which in this example by be defined by the center point c) may be less affected by the shift in pupil position. In some examples, the gaze direction GD1, GD2 may be assumed to be the same for both pupil sizes R1, R2.

Hence, the shift of the pupil center location 451, 452 may result in a change in angular offset from a first angular offset $\alpha_1$ to a second angular offset $\alpha_2$. This relation allows for the angular offset $\alpha_1$, $\alpha_2$ to be mapped against different pupil sizes R1, R2 during for example a calibration of the system, i.e., when the user watches a point in space having a known location. Based on this information, a compensation model may be formed which describes the estimated angular offset as a function of the pupil size. Alternatively, or additionally, the illumination intensity may be linked to the angular offset $\alpha_1$, $\alpha_2$ to form a similar model of the offset as a function of the illumination intensity. Preferably, such model should be calibrated to each individual user, as the iris of different users may be assumed to react differently on different illumination intensities.

In one example, the angular offset $\alpha$ for a specific pupil size may be estimated by a linear approximation. Put differently, the angular offset may be described by the following expression:

$$a(R) = kR + m$$

where $\alpha$ is the angular offset between the gaze direction GD and the eye direction ED, R is the pupil radius (preferably obtained from an image of the eye) and k and m are constants set for example during calibration. The model may be determined based on at least two measured points, e.g., a first and a second pupil size and a corresponding first and second angular offset value. It will however be appreciated that the current disclosure by no means is limited to linear approximations based on two measurements. Other models, such as higher order polynomial approximations may be used together with a data sets comprising three or more different pupil sizes and angular offsets. The following mathematical relation is an example of a higher order polynomial model:

$$\alpha(R) = \sum_{i=0}^{i=n} a_i R^i$$

were R is the pupil radius, n the polynomial degree (or order) and a the parameter set determined during the calibration.

Figure 5:
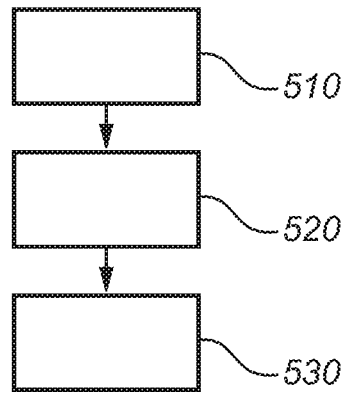
FIGS. 5-7 are flow charts of methods according to examples of the present disclosure.

FIG. 5 is a flow chart of a method according to an example of the present disclosure. The method may for example be performed by the eye tracking system 100 described above with reference to FIG. 1, or the circuitry 120 comprised in the eye tracking system 100.

The method comprises obtaining 510 a first angular offset $\alpha_1$ between a first eye direction ED1 and a first gaze direction GD1 of an eye 300 having a first pupil size R1, obtaining 520 a second angular offset $\alpha_2$ between a second eye direction ED2 and a second gaze direction GD2 of the eye 300 having a second pupil size R2, and forming 530, based on the first angular offset $\alpha 1$ and the second angular offset $\alpha 2$, a compensation model describing an estimated angular offset $\alpha$ as a function of pupil size R.

One or several of the above steps 510, 520, 530 may be performed by the circuitry 120 of the eye tracking system 100. It will be appreciated that the circuitry 120 may be integrated in a single unit, or distributed between several physically distinct units that may be arranged at different locations. Thus, according to an example, the first and second angular offsets $\alpha_1$, $\alpha_2$ may be obtained at a first circuitry unit, and then transmitted to a second circuitry unit at which the data are processed to form the compensation model.

The first and second angular offsets $\alpha_1$, $\alpha_2$ may be obtained from gaze tracking data for the eye 300, which in turn may be retrieved from an image of the eye 300. The gaze tracking data may e.g. comprise information from which the pupil center 350, the pupil size (such as e.g. radius or diameter) R, and the cornea center 314 may be derived—preferably, but not necessarily—in a similar manner as described for example in connection with FIGS. 3a and b. These images may for example be obtained from an image sensor, such as a camera, as disclosed in connection with FIG. 1. The image sensor may be arranged to capture images of the eye 300 reflecting glints from one or several illuminators 111, 112. The images may be captured at different illumination intensities, for example at different ambient light conditions, so as to obtain information representing different pupil sizes R1, R2. In one example, the images may be obtained during a calibration procedure in which the user watches known positions on for example a display. The calibration procedure may for example be a nine-point calibration procedure, in which the eye(s) of the user is/are captured when the user watches each one of nine physically separate points on the display.

Figure 6:
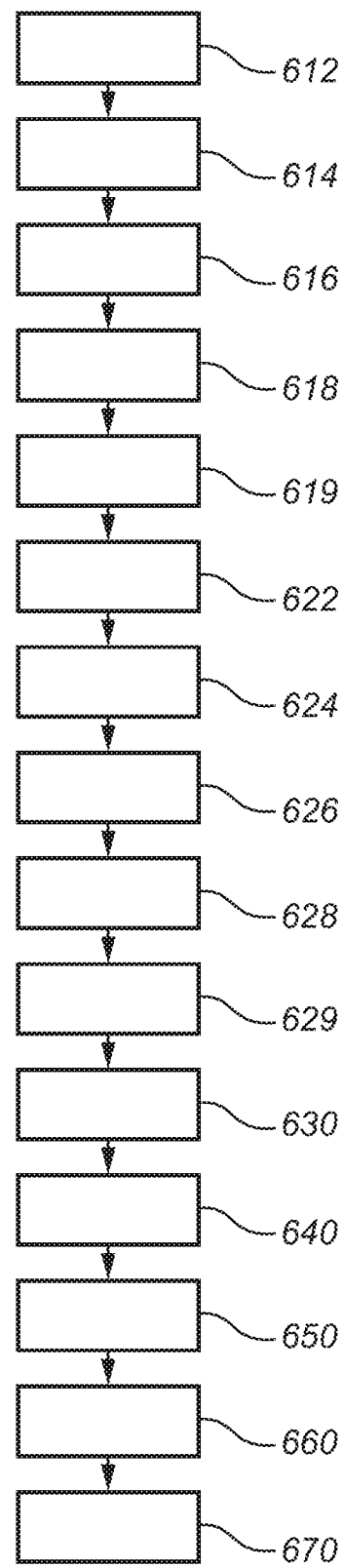

FIG. 6 is a flow chart of a method according to an example, which may be similar to the method according to the example described with reference to FIG. 5. In the present example, a first image may be acquired 612, e.g. by a image sensor of a system according to an example similar to the one discussed above in connection with FIG. 1, of the eye having a first pupil size R1. The captured image may be analyzed in order to determine 614 the first eye direction ED1 based on the location of the estimated cornea sphere center 314 and the location of the estimated pupil center 350, and to determine 616 the first gaze direction GD1 based on a known point of gaze (for example obtained from a calibration pattern) and the estimated cornea sphere center 314. Further, the pupil size R1 may be determined 618 from the same image. The first gaze direction GD1 and the first eye direction ED1 may then be used to determine 619 (e.g. by means of a processor or circuitry) the angular offset $\alpha_1$ between the two directions, and to associate the angular offset $\alpha_1$ with the specific pupil size R1 the eye when the image was captured.

The above steps 612-619 may be repeated for a second image of the eye, preferably having a second pupil size R2 differing from the first pupil size R1. Thus, the method may comprise the steps of acquiring 622 a second image of the eye, analyzing the second image to determine 624 the second eye direction ED2 based on the location of the estimated cornea sphere center 314 (this location may either be determined based on the second image, or retrieved from a prior measurement, such as e.g. the first image or previously stored calibration data), and the location of the estimated pupil center 350 (which may be assumed to differ from the estimated pupil center of the first image, given that the pupil radius varies between the two images). Further, the method may comprise the steps of determining 626 the second gaze direction GD2 based on a known point of gaze (which may be the same point as for the first image, or a different point in space) and the estimated cornea sphere center 314. The angular offset $\alpha2$ between the second gaze direction GD2 and the second eye direction ED2 may then be determined 629 and associated with the second pupil size R2, which may be determined 628 from the same image.

The first angular offset $\alpha1$, the second angular offset $\alpha2$, and the respective pupil sizes R1, R2 may in a subsequent step be used for forming 630 the compensation model describing the angular offset $\alpha$ as a function of the pupil size R. The model may for example be a linear model, a polynomial approximation or an s-curve, or a set of entries of a lookup-table. The model may be stored 640 in a storage area of the system, or sent to a storage area to which the system (or circuitry) has access. The storage area may further be adapted to store 650 the images used for obtaining the angular offsets during the calibration procedure, or storing raw data retrieved from the images, for later use. In case a further angular offset between a further eye direction and a further gaze direction of the eye, having a further pupil size, is obtained 660 from a further image of the eye, this further angular offset may be employed to update 670 the compensation model based on the previously stored raw data, the further pupil size and the further angular offset.

Thus, it will be appreciated that the present inventive concept is not limited to methods wherein only two images are used for determining angular offsets, pupil radii and the compensation model. On the contrary, the compensation model may be formed based on eye tracking data obtained from three or more images, and may further be dynamically updated during use of the eye tracking system.

Figure 7:
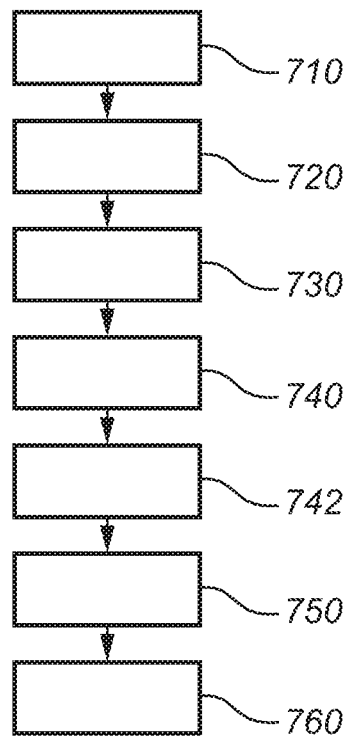

FIG. 7 is a flow chart of a method according to an example, which may be similar to the examples discussed in connection with the previous FIGS. 5 and 6. Accordingly, the method may comprise the steps of obtaining 710 a first angular offset $\alpha1$ between a first eye direction ED1 and a first gaze direction GD1 of an eye having a first pupil size R1, obtaining 720 a second angular offset $\alpha2$ between a second eye direction ED2 and a second gaze direction GD2 of the eye when the eye has a second pupil size R2, and forming 730, based on the first angular offset $\alpha1$ and the second angular offset $\alpha2$, a compensation model of the estimated angular offset $\alpha$ as a function of the pupil size R for the eye.

In a subsequent part of the method, the compensation model may be employed for tracking the gaze during use. Thus, the method according to the present example may comprise the further steps of obtaining 740 a third eye direction ED3, determining 742 the pupil size R3, and using the compensation model to determine 750 the angular offset $\alpha$ associated with the determined pupil size R3. The angular offset $\alpha$ may then be used for calculating 760 the third gaze direction GD3 of the eye. The above described steps, i.e., the steps of obtaining 740 the third eye direction, determining the pupil size 742, determining the angular offset 750 and applying the offset to the third eye direction ED3 to obtain the third gaze point GD3, may be performed repeatedly so as to achieve an active tracking of the gaze during use of the system.

Figure 8:
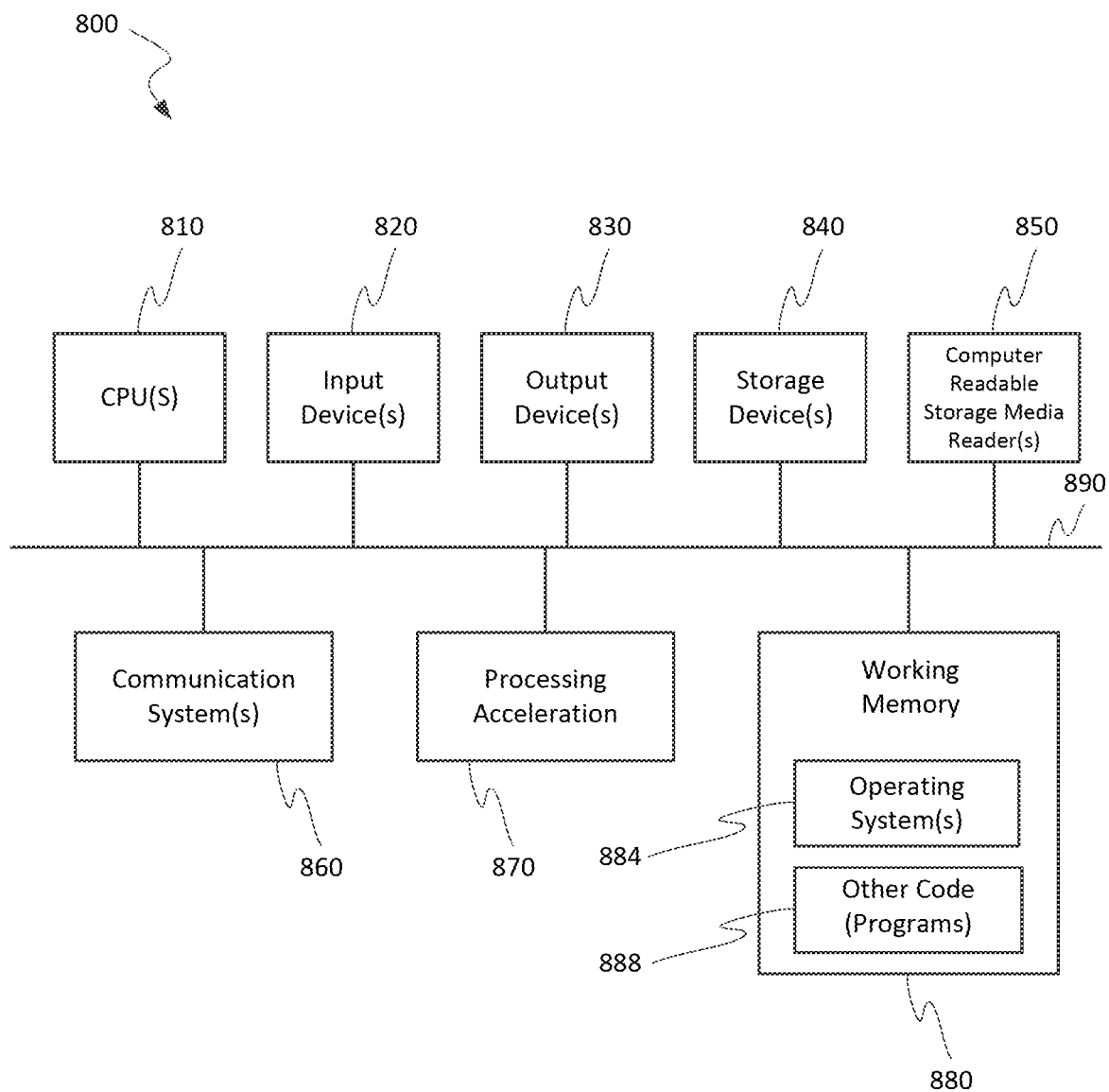
FIG. 8 is a block diagram of a specialized computer system capable of being used in at least some portion of the apparatuses or systems of the present disclosure, or implementing at least some portion of the methods of the present disclosure.

FIG. 8 is a block diagram illustrating a specialized computer system 800 in which examples of the present disclosure may be implemented. This example illustrates specialized computer system 800 such as may be used, in whole, in part, or with various modifications, to provide the functions of components described herein.

Specialized computer system 800 is shown comprising hardware elements that may be electrically coupled via a bus 890. The hardware elements may include one or more central processing units 810, one or more input devices 820 (e.g., a mouse, a keyboard, eye tracking device, etc.), and one or more output devices 830 (e.g., a display device, a printer, etc.). Specialized computer system 800 may also include one or more storage device 840. By way of example, storage device(s) 840 may be disk drives, optical storage devices, solid-state storage device such as a random access memory ("RAM") and/or a read-only memory ("ROM"), which can be programmable, flash-updateable and/or the like.

Specialized computer system 800 may additionally include a computer-readable storage media reader 850, a communications system 860 (e.g., a modem, a network card (wireless or wired), an infra-red communication device, Bluetooth™ device, cellular communication device, etc.), and working memory 880, which may include RAM and ROM devices as described above. In some examples, specialized computer system 800 may also include a processing acceleration unit 870, which can include a digital signal processor, a special-purpose processor and/or the like.

Computer-readable storage media reader 850 can further be connected to a computer-readable storage medium, together (and, optionally, in combination with storage device(s) 840) comprehensively representing remote, local, fixed, and/or removable storage devices plus storage media for temporarily and/or more permanently containing computer-readable information. Communications system 860 may permit data to be exchanged with a network, system, computer and/or other component described above.

Specialized computer system 800 may also comprise software elements, shown as being currently located within a working memory 880, including an operating system 884 and/or other code 888. It should be appreciated that alternate examples of specialized computer system 800 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of specialized computer system 800 may include code 888 for implementing any or all of the function of the various elements of the architecture as described herein. For example, software, stored on and/or executed by a specialized computer system such as specialized computer system 800, can provide the functions of components of the disclosure such as those discussed above. Methods implementable by software on some of these components have been discussed above in more detail.

Figure 9A:
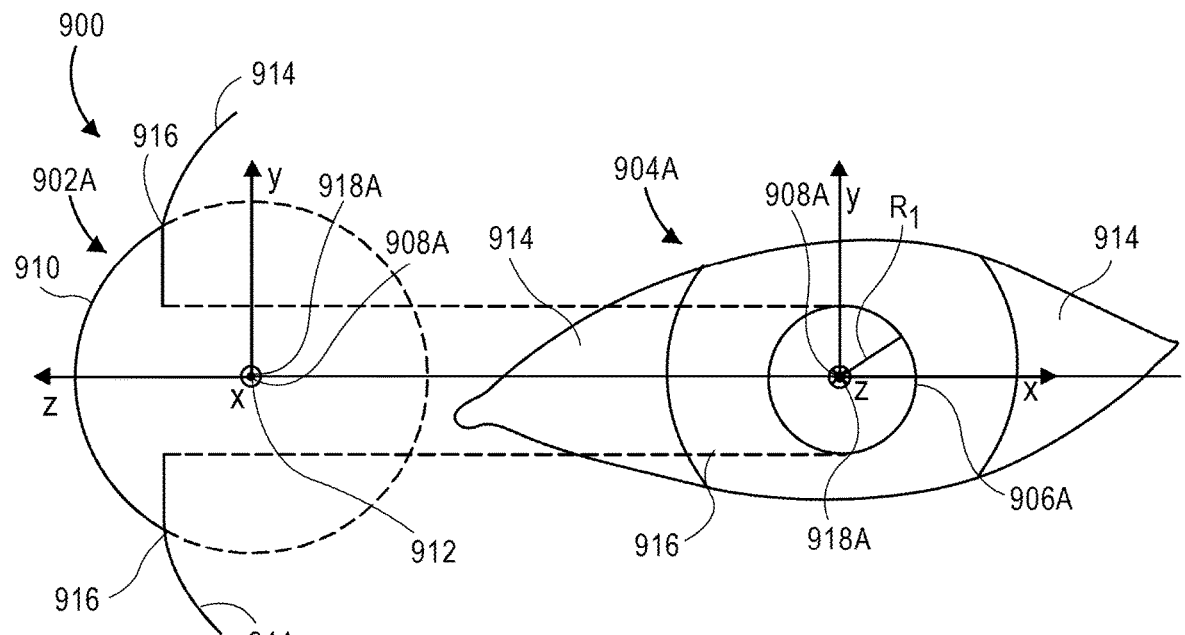
FIGS. 9a-9b are profile views and front views of an eye having varying dimensional characteristics.
Figure 9B:
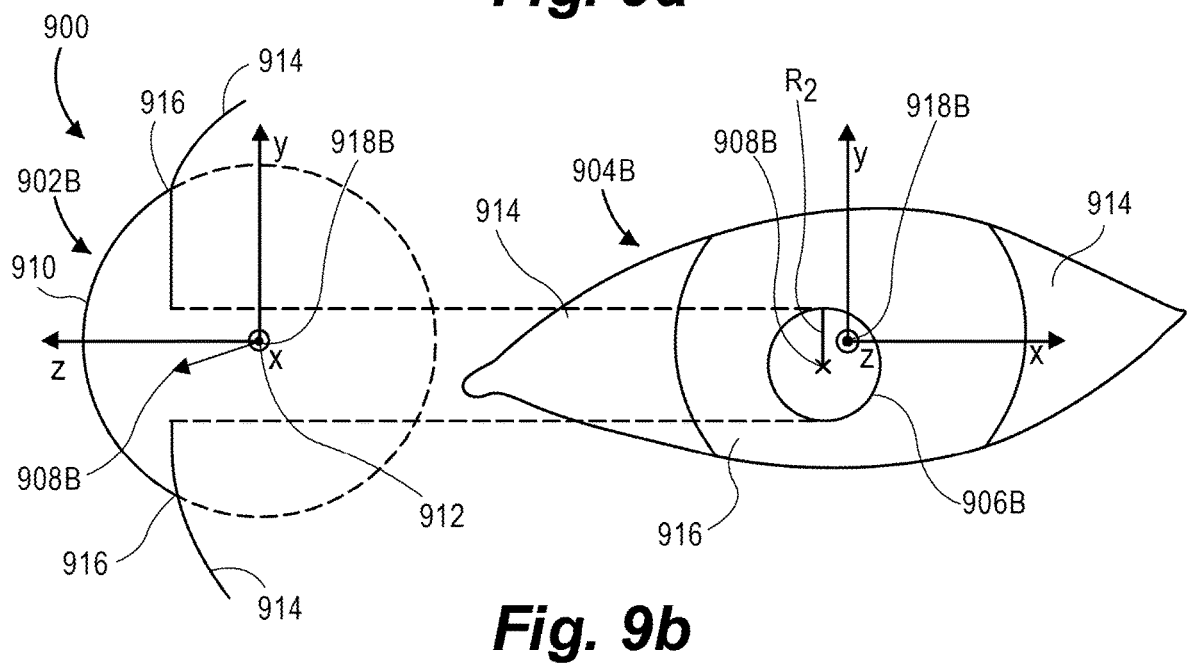

FIGS. 9a and 9b show side profile views 902A and 902B and front views 904A and 904B of an eye 900. The eye 900 includes a cornea 910, a sclera 914, and a limbus 916. The cornea 910 of eye 900 is represented by a sphere, with a three-dimensional axis having an origin 912 at the center of the cornea 910. In this example, one axis of the three-dimensional axis extends through a center of the limbus 916, having a limbus center at 918A and 918B, respectively.

As described herein, the position of a pupil 906 with respect to the limbus 916 may drift as the size of the pupil 906 changes. Generally, the average drift direction of the pupil 906 is downwards and towards the nasal plane. For example, after the pupil 906 is exposed to a bright light (resulting in pupil contraction), the pupil 906 may drift down and towards the nose.

In FIG. 9a, the pupil 906A has a first pupil size, or radius, R1. In FIG. 9b, the pupil 906B of the same eye 900 has a second pupil size, or radius, R2. In addition, the position of a pupil center 908 has changed between the views illustrated in FIGS. 9a and 9b with respect to the limbus center 918. In particular, in FIG. 9a, the pupil center 908A is aligned with the limbus center 918A (e.g., located at the same position). In FIG. 9b, the pupil center 908B is positioned below and to the left of the limbus center 918B, meaning that the pupil 906 has moved or drifted to a lower left portion of the eye 900. The movement of the pupil's 906 between FIGS. 9a and 9b has been exaggerated to illustrate the principle of pupil drift described herein.

The pupil size may for example vary with the illumination intensity. This is a known effect for applications in which the eye is exposed to for example ambient lighting, such as augmented reality applications, or a dynamic display brightness.

FIGS. 9a and 9b show an example of eye data (e.g., the limbus centers 918, the pupil centers 908, and the pupil sizes 906) that can be measured at two points in time, e.g., FIG. 9a at a first time and FIG. 9b at a second time. It should be understood that the eye data can be measured continuously (e.g., measured at many points in time according to some sampling rate), stored in memory or accessed on the fly, and used to form the offset model. In some examples, the eye data is obtained according to a sampling rate. The sampling rate may correspond to some other rate at which data about the eye is being captured. For example, the sampling rate may correspond to the frame rate at which images of the eye are being captured by an image capture device that is part of an eye tracking system. A binning mechanism can be employed to split the pupil radius ranges into bins and limit the number of samples for each bin. Samples may also be limited to frames with a moderate gaze angle, where cornea positioning in more reliable.

An offset model for compensating for changes between pupil centers 908 with respect to the limbus centers 918 as a function of pupil size 906 can be defined as follows. Let $c_p$=the pupil center 908 and $c_l$=the limbus center 918 in the eye coordinate system represented in FIGS. 9a and 9b. To measure the offset between the pupil center 908 and the limbus center 918, let y=$c_p$−$c_l$. The offset model assumes that this offset is a linear function of the pupil size 906, measured as a radius y(r)=kr+m, where k and m are (vector valued) constants. An eye tracking algorithm will observe the pupil size 906 and use this offset, y(r), to estimate the orientation of the z-axis in the eye. One goal of sampling the eye data is to estimate parameters of k and m using the linear function described herein.

To begin, eye data is used to form a set of data samples (y, r), where y=$c_p$−$c_l$ and r=pupil size 906 in terms of a pupil radius, $c_p$=pupil center 908, and $c_l$=limbus center 918. In this example, the sample (y, r) can correspond to a vector having three components ([x, y, z], r).

The eye data can be obtained using any suitable eye tracking and/or eye analysis technique. For example, the pupil centers 908 and the pupil sizes 906 can be derived from an eye tracking algorithm that estimates the cornea's position in three-dimensional space and the orientation of the eye 900. Using output from this algorithm (e.g., location and orientation of the cornea), a model of the cornea surface topology is used to project the observed limbus onto that surface. Using this projection and an algorithm that detects the limbus (e.g., edge of the iris) in an image, the position of the limbus center 918 can be obtained.

The eye data can be used to form and/or adjust a set of parameters (k and m) of an offset model. As the eye data continues to grow (e.g., as more samples are measured over time), the samples of (y, r) will continue to grow. Statistical methods can be used to determine when to adjust an active offset model. For example, an appropriate time for adjusting the active offset model can be when it can be determined with a high degree of probability that the values of k and m implied by the collected samples (y, r) are different from the estimates of k and m in the active offset model.

The estimation of k and m can done by least squares fitting to the collected samples. The fitting can also be done in a maximum a-posterior way, if a prior on the expected value of the parameters is known. This can be especially important for the z-components of the offset, how "deep" the pupil is inside the eye.

At some point, the user will calibrate the eye tracking algorithm. The calibration can compensate for an incorrect pupil offset, but only if the offset is constant. To deal with this problem, any update to the offset model y(r) may change the value of the offset that was active during the calibration. Since the pupil radius may vary during the calibration, this requirement cannot be met exactly, so it is enforced in a least-squares sense. Let k and m be the estimated parameters, $k_m$ and $m_c$ the parameters that were active during the calibration and $\{r_c\}$ the set of radii during calibration. Then the estimate of m is adjusted as follows:

$$m := \arg\min_m \text{sum}\_\{r_c\}((kr_c+m)-(k_c r_c+m_c))^2$$

FIGS. 10a-10c illustrate example graphs representing components (e.g., x, y, and z components) of position vectors corresponding to the pupil center 908 and the limbus center 918. FIG. 10d illustrates an example of a linear regression approach for graphing the offset model as a linear function, y(r)=kr+m.

In FIG. 10a, position in the x-axis (of the three-dimensional axis represented in FIG. 9 which is an eye-fixed coordinate system) is compared to radius of the pupil. The position of the limbus center, represented by the "+", more or less stays the same as the radius value increases. The position of the pupil center in the x-axis, represented by the "×", changes as the radius value increases.

In FIG. 10b, position in the y-axis (of the three-dimensional axis represented in FIG. 9) is compared to radius of the pupil. The position of the limbus center, represented by the "+", more or less stays the same as the radius value increases. The position of the pupil center in the y-axis, represented by the "×", changes as the radius value increases.

In FIG. 10c, position in the z-axis (of the three-dimensional axis represented in FIG. 9) is compared to radius of the pupil. The position of the limbus center, represented by the "+", more or less stays the same as the radius value increases. The position of the pupil center in the z-axis, represented by the "×", changes as the radius value increases.

In FIG. 10d, the components of the position vectors are graphed. In essence, FIG. 10d represents a combination of the graphs from FIGS. 10a-10c. A linear regression technique has been used to graph line 1010. The line 1010 corresponds to the linear function that is an example of the offset model described herein.

Figure 11:
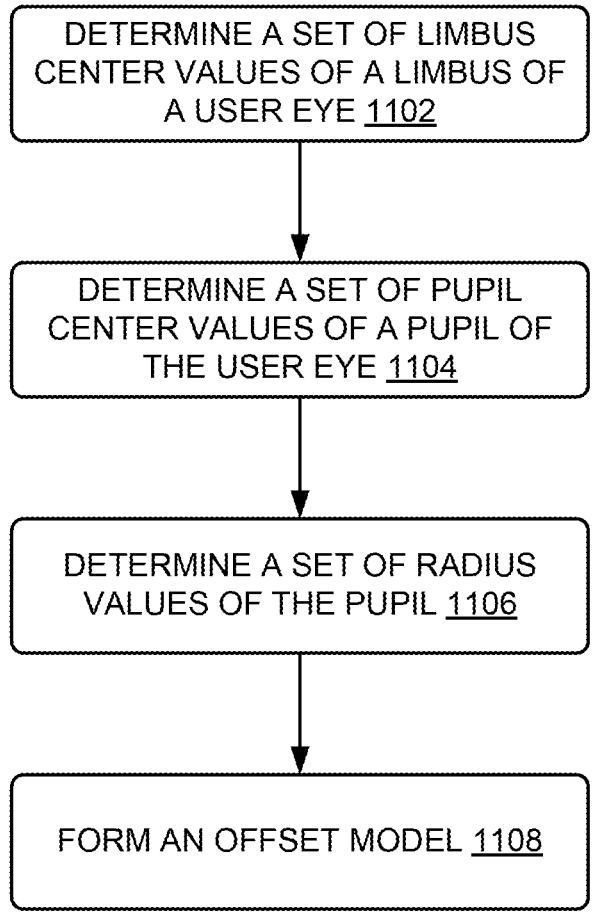
FIG. 11 is a flow chart of methods according to examples of the present disclosure.
Figure 12:
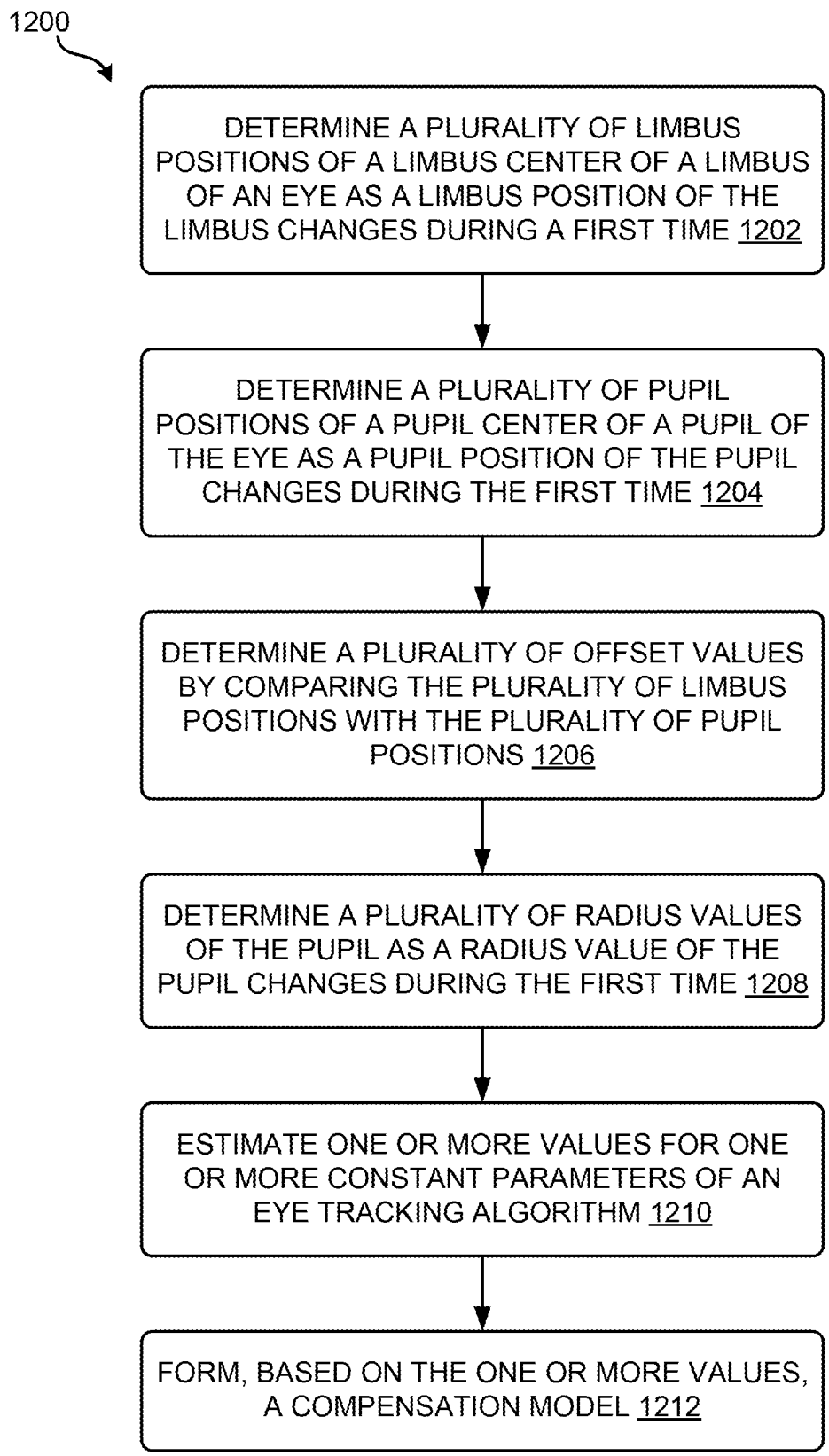
FIG. 12 is a flow chart of methods according to examples of the present disclosure.

FIGS. 11 and 12 illustrate example flow diagram showing processes 1100 and 1200, according to at least a few examples. These processes, and any other processes described herein, is illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

FIG. 11 illustrates an example flow diagram showing the process 1100 for forming an offset model, according to at least one example. The process 1100 may be performed by the computer system 800 and/or the eye tracking system 100.

The process 1100 may begin at 1102 by determining a set of limbus center values of a limbus of a user eye. The set of limbus center values can be determined at a sampling rate. In some examples, the set of limbus center values is determined at a predefined set of time values (e.g., every 20 milliseconds, every 10 milliseconds, or even much faster). The set of limbus center values can be determined with respect to a three-dimensional coordinate system with an origin at an estimated center of a cornea of the user eye. The set of limbus center values may correspond to the location of a center point of the limbus as projected at an exterior surface of the user eye (e.g., within the cornea) or further within the eye. In some examples, the set of limbus center values is determined for two user eyes. Each limbus center values can be represented as a vector having three components, an x-component, a y-component, and a z-component. In some examples, the limbus center values may correspond to $c_l$ in the equation $y=c_p-c_l$.

At 1104, the process 1100 includes determining a set of pupil center values of a pupil of the user eye. The set of pupil center values can be determined according to the sampling rate, e.g., the same sampling rate at which the set of limbus center values is determined. The set of pupil center values can be determined with respect to the three-dimensional coordinate system described herein. The set of pupil center values may represent the location of a center point of the pupil at an exterior surface of the eye or within the eye. In some examples, the set of pupil center values is determined for two user eyes. Each pupil center value can be represented as a vector having three components, an x-component, a y-component, and a z-component. In some examples, the pupil center values may correspond to $c_p$ in the equation $y=c_p-c_l$.

At 1106, the process 1100 includes determining a set of radius values of the pupil. The set of radius values can be determined according to the sampling rate, e.g., the same sampling rate at which the set of limbus center values and the set of pupil center values are determined. In this manner, individual radius values may be measured at the same time that corresponding limbus center values and pupil center values are measured. The set of radius values represent sizes of the pupil. In some examples, the radius values may correspond to r described herein.

At 1108, the process 1100 includes forming an offset model. Forming the offset model can include doing so based on (i) the set of limbus center values, (ii) the set of pupil center values, and (iii) the set of radius values. For example, forming the offset model can include using the set of limbus center values, the set of pupil center values, and the set of radius values to determine a line that fits this data in the form $y(r)=kr+m$. In some examples, the offset model describes an estimated offset between a limbus center and a pupil center as a function of pupil size.

In an example, determining the set of limbus center values includes measuring a first limbus center value at a first time and measuring a second limbus center value at a second time. In this example, determining the set of pupil center values includes measuring a first pupil center value at the first time and measuring a second pupil center value at the second time. In this example, determining the set of radius values includes measuring a first radius value at the first time and measuring a second radius value at the second time.

In some examples, determining the set of limbus center values, determining the set of pupil center values and determining the set of radius values are performed at least while an eye tracking system tracks the user eye. In this manner, the process 1100 for forming the offset model can be performed for continuous calibration of the eye tracking system.

In an example, the offset model includes a linear function. In this example, forming the offset model includes estimating one or more constant values of the linear function based on a linear regression technique. In this examples, a first constant value of the one or more constant values corresponds to k parameter of the linear function that represents a slope of the linear function. In this example, a second constant value of the one or more constant values corresponds to m parameter of the linear function. The m parameter can represent an intersection point of the linear function.

In an example, the process 1100 further includes determining a set of offset values by comparing the set of limbus center values with the set of pupil center values. In this example, each offset value represents an offset between a respective pupil position with respect to a respective limbus position. In this example, forming the offset model is further based on the set of offset values. Comparing the set of limbus center values with the set of pupil center values may include subtracting the set of limbus center values from the set of limbus pupil values (e.g., $y=c_p-c_l$).

In some examples, forming the offset model includes updating one or more constant values of an existing offset model to define the offset model.

In some examples, the process 1100 further includes using an eye tracking algorithm to track the user eye based on the offset model. In some examples, the eye tracking algorithm may be implemented at an eye tracking device such as the eye tracking device 100.

In some examples, prior to forming the offset model, the process 1100 further includes estimating one or more values for one or more constant parameters of an eye tracking algorithm by at least: graphing the set of offset values and the set of radius values, and estimating the one or more values for the one or more constant parameters based on a linear approximation of the set of offset values and the set of radius values. For example, such estimating can include using a least squares form of linear approximation to define a line of the form $y(r)=kr+m$.

FIG. 12 illustrates an example flow diagram showing the process 1200 for forming an offset model, according to at least one example. The process 1200 may be performed by the computer system 800 and/or the eye tracking system 100.

The process 1200 may begin at 1202 by determining a plurality of limbus positions of a limbus center of a limbus of an eye as a limbus position of the limbus changes during a first time.

At 1204, the process 1200 includes determining a plurality of pupil positions of a pupil center of a pupil of the eye as a pupil position of the pupil changes during the first time.

At 1206, the process 1200 includes determining a plurality of offset values by comparing the plurality of limbus positions with the plurality of pupil positions, each offset value representing an offset between a respective pupil position with respect to a respective limbus position.

At 1208, the process 1200 includes determining a plurality of radius values of the pupil as a radius value of the pupil changes during the first time.

At 1210, the process 1200 includes estimating one or more values for one or more constant parameters of an eye tracking algorithm. This can be performed by at least: graphing the plurality of offset values and the plurality of radius values, and estimating the one or more values for the one or more constant parameters based on a linear approximation of the plurality of offset values and the plurality of radius values.

At 1212, the process 1200 includes forming, based on the one or more values, a compensation model describing an estimated offset between a limbus center of the limbus and a pupil center of the pupil as a function of pupil size.

The person skilled in the art realizes that the present disclosure is by no means limited to the preferred examples described above. On the contrary, may modifications and variations are possible within the scope of the appended claims. For example, the person skilled in the art realizes that the eye/gaze tracking methods described herein may be performed by many other eye/gaze tracking systems than the eye/gaze tracking system 100 shown in FIG. 1, for example using multiple illuminators and multiple cameras.

Additionally, variation to the disclosed examples can be understood and effected by those skilled in the art in practicing the claimed disclosure, from a study of the drawings, the disclosure, and the appended claims. In the claims, the word "comprising" does not exclude other elements or steps, and the indefinite article "a" or "an" does not exclude a plurality. The division of tasks between functional units referred to in the present disclosure does not necessarily correspond to the division into physically distinct units; to the contrary, a physical component may have multiple functionalities, and a task may be carried out in a distributed fashion, by several physical components in cooperation. A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

The mere fact that certain measures/features are recited in mutually different dependent claims does not indicate that a combination of these measures/features cannot be used to advantage. Method steps need not necessarily be performed in the order in which they appear in the claim or in the examples described herein, unless it is explicitly described that a certain order is required. Any reference signs in the claims should not be construed as limiting the scope.

What is claimed is:

1. A computer-implemented method, comprising:
    determining, according to a sampling rate, a set of limbus center values of a limbus of a user eye;
    determining, according to the sampling rate, a set of pupil center values of a pupil of the user eye;
    determining, according to the sampling rate, a set of radius values of the pupil; and
    forming an offset model based on (i) the set of limbus center values, (ii) the set of pupil center values, and (iii) the set of radius values, the offset model describing an estimated offset between a limbus center and a pupil center as a function of pupil size.

2. The computer-implemented method of claim 1, wherein:
    determining the set of limbus center values comprises measuring a first limbus center value at a first time and measuring a second limbus center value at a second time;
    determining the set of pupil center values comprises measuring a first pupil center value at the first time and measuring a second pupil center value at the second time; and
    determining the set of radius values comprises measuring a first radius value at the first time and measuring a second radius value at the second time.

3. The computer-implemented method of claim 1, wherein determining the set of limbus center values, determining the set of pupil center values and determining the set of radius values are performed at least while an eye tracking system tracks the user eye.

4. The computer-implemented method of claim 1, wherein:
    the offset model comprises a linear function; and
    forming the offset model comprises estimating one or more constant values of the linear function based on a linear regression technique.

5. The computer-implemented method of claim 4, wherein:
a first constant value of the one or more constant values corresponds to "k" parameter of the linear function that represents a slope of the linear function; and
a second constant value of the one or more constant values corresponds to "m" parameter of the linear function, the "m" parameter that represents an intersection point of the linear function.

6. The computer-implemented method of claim 1, wherein:
the method further comprises determining a set of offset values by comparing the set of limbus center values with the set of pupil center values, each offset value representing an offset between a respective pupil position with respect to a respective limbus position; and
forming the offset model is further based on the set of offset values.

7. The computer-implemented method of claim 1, wherein forming the offset model comprises updating one or more constant values of an existing offset model to define the offset model.

8. The computer-implemented method of claim 1, further comprising using an eye tracking algorithm to track the user eye based on the offset model.

9. A system, comprising:
a memory configured to store computer-executable instructions; and
a processor configured to access the memory and execute the computer-executable instructions to at least:
determine a set of limbus center values of a limbus of a user eye;
determine a set of pupil center values of a pupil of the user eye;
determining a set of radius values of the pupil; and
forming an offset model based on (i) the set of limbus center values, (ii) the set of pupil center values, and (iii) the set of radius values, the offset model describing an estimated offset between a limbus center and a pupil center as a function of pupil size.

10. The system of claim 9, wherein:
determining the set of limbus center values comprises measuring a first limbus center value at a first time and measuring a second limbus center value at a second time;
determining the set of pupil center values comprises measuring a first pupil center value at the first time and measuring a second pupil center value at the second time; and
determining the set of radius values comprises measuring a first radius value at the first time and measuring a second radius value at the second time.

11. The system of claim 9, wherein:
the processor is further configured to determine a set of offset values by comparing the set of limbus center values with the set of pupil center values, each offset value representing an offset between a respective pupil position with respect to a respective limbus position; and
forming the offset model is further based on the set of offset values.

12. The system of claim 9, wherein determining the set of limbus center values, determining the set of pupil center values, and determining the set of radius values are performed at a sampling rate.

13. The system of claim 9, wherein:
the offset model comprises a linear function; and
forming the offset model comprises estimating one or more constant values of the linear function based on a linear regression technique.

14. The system of claim 13, wherein:
a first constant value of the one or more constant values corresponds to "K" parameter of the linear function that represents a slope of the linear function; and
a second constant value of the one or more constant values corresponds to "M" parameter of the linear function, the "M" parameter that represents an intersection point of the linear function.

15. One or more computer-readable storage devices comprising computer-executable instructions that, when executed by one or more processors, cause the one or more processors to perform operations comprising:
determining a set of limbus center values of a limbus of a user eye;
determining a set of pupil center values of a pupil of the user eye;
determining a set of radius values of the pupil; and
forming an offset model based on (i) the set of limbus center values, (ii) the set of pupil center values, and (iii) the set of radius values, the offset model describing an estimated offset between a limbus center and a pupil center as a function of pupil size.

16. The one or more computer-readable storage devices of claim 15, wherein the operations further comprise determining a set of offset values by comparing the set of limbus center values with the set of pupil center values, each offset value representing an offset between a respective pupil center value with respect to a respective limbus center value.

17. The one or more computer-readable storage devices of claim 16, wherein the operations further comprise, prior to forming the offset model, estimating one or more values for one or more constant parameters of an eye tracking algorithm by at least:
graphing the set of offset values and the set of radius values; and
estimating the one or more values for the one or more constant parameters based on a linear approximation of the set of offset values and the set of radius values.

18. The one or more computer-readable storage devices of claim 15, wherein:
determining the set of limbus center values comprises measuring a first limbus center value at a first time and measuring a second limbus center value at a second time;
determining the set of pupil center values comprises measuring a first pupil center value at the first time and measuring a second pupil center value at the second time; and
determining the set of radius values comprises measuring a first radius value at the first time and measuring a second radius value at the second time.

19. The one or more computer-readable storage devices of claim 15, wherein determining the set of limbus center values, determining the set of pupil center values and determining the set of radius values are performed at least while an eye tracking system tracks the user eye.

20. The one or more computer-readable storage devices of claim 15, wherein the operations further comprise using an eye tracking algorithm to track the user eye based on the offset model.

* * * * *